United States Patent

Richardson et al.

[11] Patent Number: 4,518,604
[45] Date of Patent: May 21, 1985

[54] ANTIFUNGAL 1-ARYL-2-(1H-1,2,4-TRIAZOL-1YL)-1-PERFLUOROALKYLETHYL HALIDES

[75] Inventors: Kenneth Richardson; Peter J. Whittle, both of Canterbury, England

[73] Assignee: Pfizer Inc., New York, N.Y.

[21] Appl. No.: 546,128

[22] Filed: Oct. 27, 1983

Related U.S. Application Data

[63] Continuation-in-part of Ser. No. 517,141, Jul. 25, 1983, abandoned.

[51] Int. Cl.³ .................. A01N 43/64; A61K 31/41; C07D 249/08; C07D 401/06
[52] U.S. Cl. .................. 514/340; 546/276; 546/268; 548/262; 549/559; 549/563; 514/383
[58] Field of Search .............. 548/262; 546/276; 424/269, 263

[56] References Cited

FOREIGN PATENT DOCUMENTS 15756 9/1980 European Pat. Off. .
47594 3/1982 European Pat. Off. .
48548 3/1982 European Pat. Off. .
60223 9/1982 European Pat. Off. ............ 548/262

Primary Examiner—Alton D. Rollins
Attorney, Agent, or Firm—Charles J. Knuth; Albert E. Frost; Paul D. Thomas

[57] ABSTRACT

Compounds of the formula

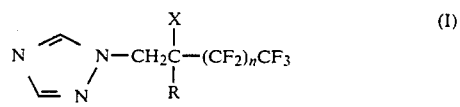

or a pharmaceutically or agriculturally acceptable acid addition salt thereof wherein R is 5-chloro-2-pyridyl, phenyl or phenyl substituted by from 1 to 3 substituents selected from F, Cl, Br, I, $CF_3$, ($C_1$–$C_4$)-alkyl and ($C_1$–$C_4$)alkoxy; X is a halogen atom, and n is zero or an integer from 1 to 5, method for their use in combatting fungal infections in plants, seeds and animals, including humans, and pharmaceutical and agricultural compositions containing them.

14 Claims, No Drawings

ANTIFUNGAL 1-ARYL-2-(1H-1,2,4-TRIAZOL-1YL)-1-PERFLUOROALKYLETHYL HALIDES

CROSS REFERENCE TO RELATED APPLICATION

This application is a continuation-in-part of copending application Ser. No. 517,141 filed July 25, 1983, abandoned.

BACKGROUND OF THE INVENTION

This invention relates to novel triazole derivatives having antifungal activity which are useful in the treatment of fungal infections in animals, including humans, and as agricultural fungicides.

Published European Patent Application Nos. 15,756; 47,594 and 48,548 disclose triazole compounds of the formula

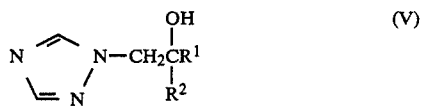

wherein $R^1$ is alkyl, cycloalkyl or optionally substituted phenyl and $R^2$ is phenyl or benzyl, each of which is optionally substituted, e.g. with halogen; methods for their use as plant fungicides and plant growth regulators, and pharmaceutical and veterinary compositions containing them.

Published European Patent Application No. 69,442 discloses difluorophenyl-1,3-bis-triazolylpropan-2-ol having antifungal activity.

SUMMARY OF THE INVENTION

According to the invention, there are provided compounds of the formula

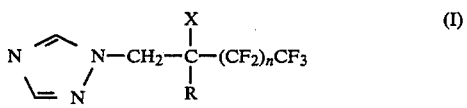

where R is phenyl optionally substituted by 1 to 3 substituents each independently selected from F, Cl, Br, I, $CF_3$, $(C_1-C_4)$alkyl and $(C_1-C_4)$alkoxy, or R is a 5-chloropyrid-2-yl group; X is F, Cl or Br; and n is zero or an integer from 1 to 5; or their pharmaceutically or agriculturally acceptable acid addition salts.

$C_3$ and $C_4$ alkyl and alkoxy groups can be straight or branched chain.

The invention also provides a pharmaceutical composition comprising an antifungal amount of a compound of the formula (I) or a pharmaceutically acceptable acid addition salt thereof, together with a pharmaceutically acceptable diluent or carrier.

The invention further provides a compound of the formula (I) or a pharmaceutically acceptable acid addition salt thereof, for use in treating fungal infections in animals, including humans.

The invention yet further provides an agricultural composition suitable for use on a plant comprising an antifungal amount of a compound of the formula (I) or an agriculturally acceptable acid addition salt thereof, together with an agriculturally acceptable diluent or carrier.

The invention yet further provides a method of treating an animal, including a human being, having a fungal infection, which comprises treating said animal with an antifungal effective amount of a compound of the formula (I) or pharmaceutically acceptable acid addition salt thereof.

When R is said optionally substituted phenyl group, it is preferably phenyl substituted by 1 to 3 substituents, more preferably 1 or 2 substituents, each independently selected from F, Cl, Br, I and $CF_3$. The more preferred individual groups represented by R are 4-fluorophenyl, 4-chlorophenyl, 4-bromophenyl, 4-iodophenyl, 4-trifluoromethylphenyl, 2-chlorophenyl, 2-fluorophenyl, 2,4-dichlorophenyl, 2,4-difluorophenyl, 2,5-difluorophenyl, 2-fluoro-4-chlorophenyl, 2,4,6-trifluorophenyl and 4-bromo-2,5-difluorophenyl. Most preferably, R is 2,4-difluorophenyl, 4-chlorophenyl or 4-fluorophenyl.

Particularly preferred values of n are zero, 1 and 2; most particularly preferred n is zero.

X is preferably Cl.

Thus, especially preferred invention compounds are:
1-[2-chloro-2-(2,4-difluorophenyl)-3,3,3-trifluoropropyl]-1H-1,2,4-triazole,
1-[2-chloro-2-(4-chlorophenyl)-3,3,3-trifluoropropyl]-1H-1,2,4-triazole,
1-[2-chloro-2-(4-fluorophenyl)-3,3,3-trifluoropropyl]-1H-1,2,4-triazole,
1-[3-chloro-3-(4-fluorophenyl)-1,1,1,2,2-pentafluorobutan-4-yl]-1H-1,2,4-triazole, and
1-[4-chloro-4-(2,4-difluorophenyl)-1,1,1,2,2,3,3-heptafluoropentan-5-yl]-1H-1,2,4-triazole.

DETAILED DESCRIPTION OF THE INVENTION

The compounds of the formula (I) are prepared, e.g., by halogenation of the corresponding hydroxy compounds of the formula:

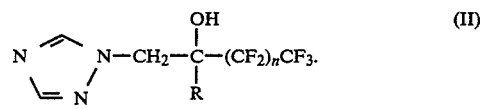

The halogenation is carried out according to conventional procedures, e.g. using $SOCl_2$, $SOBr_2$ or diethylaminosulphur trifluoride ($Et_2NSF_3$) as appropriate.

In a typical procedure utilizing thionyl chloride or bromide, the propanol (II) in a suitable solvent, e.g. dry acetonitrile, is reacted with thionyl chloride or bromide in the presence of a base, e.g. imidazole. The reaction ordinarily proceeds to completion at room temperature although in some cases heating at a temperature of from about 40° C. up to the reflux temperature may be necessary to accelerate the reaction. The product can be recovered and purified by conventional procedures, as described in the Examples.

The reaction using diethylaminosulphur trifluoride is typically carried out at about 0° C. in methylene chloride as the solvent.

The starting compounds of formula (II) are the subject of our copending U.S. patent application Ser. No. 517,183 filed concurrently with our parent application on July 25, 1983, and are prepared by the methods described in the former application.

These methods include reaction of an oxirane of the formula:

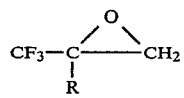 (III)

where R is as defined for formula (I), with 1,2,4-triazole, preferably in the presence of a base, e.g. K₂CO₃. Alternatively an alkali metal salt of 1,2,4-triazole can be used, preparable e.g. from 1,2,4-triazole and NaH. Typically the reaction is carried out by heating the reactants together at a temperature of from about 50° up to 120° C. in a suitable organic solvent, e.g. dimethylformamide, for up to about 24 hours. The product can then be isolated and purified conventionally.

The oxiranes (III) are obtainable conventionally, generally from the ketones of the formula:

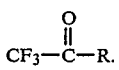 (IV)

This can be achieved by the reaction of (IV) with dimethyloxosulphonium methylide prepared from trimethylsulphoxonium iodide and either (a) sodium hydride in dimethylsulphoxide, or (b) cetrimide (cetyltrimethylammonium bromide) and sodium hydroxide in a mixture of water and toluene or water and 1,1,1-trichloroethane. The reaction using sodium hydride is typically carried out by stirring sodium hydride with trimethylsulphoxonium iodide at, e.g., room temperature. Dimethylsulphoxide (DMSO) is then added dropwise and the mixture stirred for about 30 minutes, after which time the ketone (IV) is added in DMSO. The desired product is generally obtained by stirring at room temperature for about an hour. The reaction using cetrimide is typically achieved by stirring the ketone (IV), trimethylsulphoxonium iodide and cetrimide in a mixture of 1,1,1-trichloroethane and aqueous sodium hydroxide solution for about 2 hours at, e.g. 70°-100° C. While in either case the oxirane product (III) can be isolated, if desired, it is often more convenient to convert this in situ to the desired product.

The ketones (IV) are either known compounds or can be prepared conventionally, e.g.:

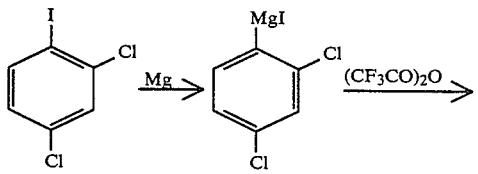

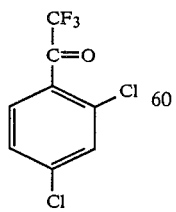

The compounds of the formula (II) where n is zero can also be prepared by conventional procedures as follows:

CF₃COCH₂.Hal +

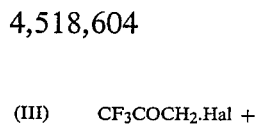

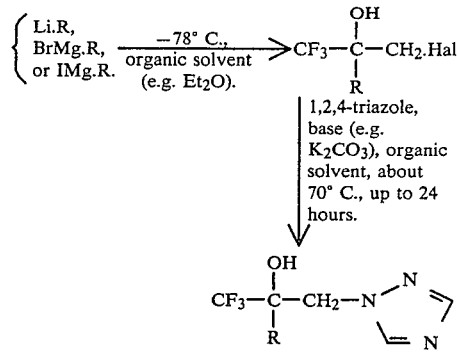

"Hal"=Cl or Br.

Again an alkali metal salt of the triazole can be used in place of 1,2,4-triazole/K₂CO₃.

In a typical procedure, the halo-ketone and the lithio or Grignard reagent are stirred together in e.g. diethylether at −78° C. for about one hour. The intermediate halo-alkanol is then recovered conventionally, if desired. The halo-alkanol and 1,2,4-triazole are then heated in e.g. dimethylformamide at about 50°–130° C., in the presence of a base such as potassium carbonate for up to about 24 hours. The product is then recovered in a conventional manner.

The compounds of the formula (II) in which n is an integer of from 1 to 5 are prepared, e.g., as follows:

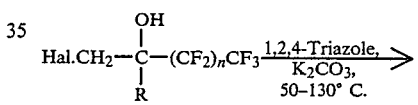

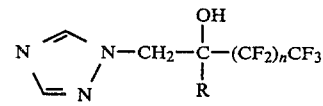

[Hal=Cl or Br and n is 1 to 5].

The reaction is typically carried out by heating in dimethylformamide at up to 130° C. for up to about 24 hours. Again the product can be recovered in a conventional manner. Again the starting materials are preparable conventionally, e.g., by the method of J. Am. Chem. Soc., 78, 2268-70 (1956):

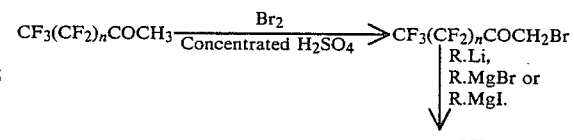

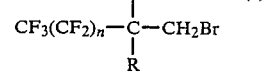 (a)

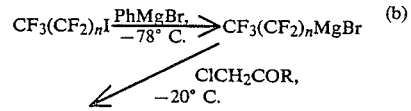 (b)

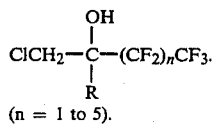

$(n = 1 \text{ to } 5)$.

All the compounds of formula (I) contain an optically active center and the invention includes both the resolved and unresolved forms.

Pharmaceutically acceptable acid addition salts of the compounds of the formula (I) are those formed from strong acids which form non-toxic acid addition salts, such as hydrochloric, hydrobromic, sulphuric, oxalic and methanesulphonic acids.

The salts may be obtained by conventional procedures, e.g. by mixing solutions containing equimolar amounts of the free base and desired acid, and the required salt is collected by filtration, if insoluble, or by evaporation of the solvent.

The compounds of the formula (I) and their pharmaceutically acceptable salts are antifungal agents, useful in combatting fungal infections in animals, including humans. For example they are useful in treating topical fungal infections in man caused by, among other organisms, species of Candida, Trichophyton, Microsporum or Epidermophyton, or in mucosal infections caused by *Candida albicans* (e.g thrush and vaginal candidiasis). They may also be used in the treatment of systemic fungal infections caused by, for example, *Candida albicans, Cryptococcus neoformans, Aspergillus fumigatus,* Coccidioides, Paracoccidioides, Histoplasma or Blastomyces.

The in vitro evaluation of the antifungal activity of the compounds can be performed by determining the minimum inhibitory concentration (m.i.c.) which is the concentration of the test compound in a suitable medium at which growth of the particular microorganism fails to occur. In practice, a series of agar plates, each having the test compound incorporated at a particular concentration is inoculated with a standard culture of, for example, *Candida albicans* and each plate is then incubated for 48 hours at 37° C. The plates are then examined for the presence or absence of growth of the fungus and the appropriate m.i.c. value is noted. Other microorganisms used in such tests can include *Cryptococcus neoformans, Aspergillus fumigatus, Trichophyton* spp, *Microsporum* spp, *Epidermophyton floccosum, Coccidioides immitis* and *Torulopsis glabrata.*

The in vivo evaluation of the compounds can be carried out at a series of dose levels by intraperitoneal or intravenous injection or by oral administration, to mice which are inoculated with a strain of *Candida albicans*. Activity is based on the survival of a treated group of mice after the death of an untreated group of mice following 48 hours observation. The dose level at which the compound provides 50% protection against the lethal effect of the infection, the $PD_{50}$ in mg/kg, is noted.

Using the above test method, the following $PD_{50}$ values (mg/kg) were obtained with selected compounds of the invention in mice infected with *Candida albicans*:

| Compound of Example No. | Oral $PD_{50}$ (mg/kg) |
| --- | --- |
| 1 | 0.15 |
| 2 | 0.6 |
| 3 | 0.6 |
| 4 | <0.1 |
| 5 | <0.1 |

For human use, the antifungal compound of formula (I), or a pharmaceutically acceptable acid addition salt thereof, can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs or suspensions containing flavoring or coloring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the antifungal compounds of the formula (I) will be from 0.1 to 10 mg/kg (in divided doses) when administered by either the oral or parenteral route. Thus tablets or capsules of the compounds will contain from 5 mg to 0.5 g of active compound for administration singly or two or more at a time as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the antifungal compounds of the formula (I) can be administered in the form of a suppository or pessary, or they can be applied topically in the form of a lotion, solution, cream, ointment or dusting powder. For example, they can be incorporated into a cream consisting of an aqueous emulsion of polyethylene glycols or liquid paraffin; or they can be incorporated, at a concentration of from 1 to 10%, into an ointment consisting of a white wax or white soft paraffin base together with such stabilizers and preservatives as may be required.

The compounds of the formula (I) and their salts also have activity against a variety of plant pathogenic fungi, including for example various rusts, mildews and moulds, and the compounds are thus useful for treating plants and seeds to eradicate or prevent such diseases.

The in vitro evaluation of the activity of the compounds against plant fungi can be determined by measuring their minimum inhibitory concentrations in the same way as previously described except that the plates are incubated at 30° C. for 48 hours or longer before being examined for the presence or absence of growth.

Microoorganisms used in such tests include *Cochliobolus carbonum, Pyricularia oryzae, Glomerella cingulata, Penicillium digitatum, Botrytis cinerea* and *Rhizoctonia solani.*

For agricultural and horticultural purposes the compounds and their agriculturally acceptable acid addition salts are preferably used in the form of a composition formulated as appropriate to the particular use and purpose desired. Thus the compounds may be applied in the form of dusting powders, or granules, seed dressings, aqueous solutions, dispersions or emulsions, dips, sprays, aerosols or smokes. Compositions may also be supplied in the form of dispersible powders, granules or grains, or concentrates for dilution prior to use. Such compositions may contain such conventional carriers, diluents or adjuvants as are known and acceptable in agriculture and horticulture and they are manufactured in accordance with conventional procedures. The compositions may also incorporate other active ingredients, for example, compounds having herbicidal or insecticidal activity or a further fungicide. The compounds and compositions can be applied in a number of ways, for example they can be applied directly to the plant foliage, stems, branches, seeds or roots or to the soil.

The following Examples illustrate the invention. All temperatures are in °C. Ratios of solvent mixtures are by volume. Percentages are by weight unless otherwise noted.

EXAMPLE 1

1-[2-Chloro-2-(2,4-difluorophenyl)-3,3,3-trifluoropropyl]-1H-1,2,4-triazole

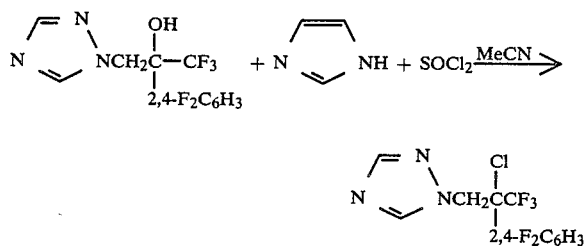

Imidazole (0.53 g, 7.8 mmole) was dissolved in dry acetonitrile (4 ml) and thionyl chloride (0.3 ml, 4.1 mmole) was added dropwise over 2 minutes followed by a solution of 2-(2,4-difluorophenyl)-1-(1H-1,2,4-triazol-1-yl)-3,3,3-trifluoropropan-2-ol (0.389 g, 1.25 mmole) in dry acetonitrile (12 ml). The mixture was stirred at room temperature for 24 hours and then heated to 70° C. for ½ hour. The cooled mixture was then poured into sodium bicarbonate solution and extracted with dichloromethane (3×100 ml). The combined dichloromethane extracts were washed once with water, dried over magnesium sulphate and evaporated. Chromatography of the residue on silica (230–400 mesh), eluting with 40:60 (by volume) ethyl acetate:hexane gave, after recrystallization from ethyl acetate/hexane, the title compound, 170 mg (41%), m.p. 87°–88° C.

Analysis %: Found: C, 42.4; H, 2.3; N, 13.4. $C_{11}H_7ClF_5N_3$ requires: C, 42.4; H, 2.3; N, 13.5.

EXAMPLES 2 TO 5

The compounds of these Examples were prepared similarly to Example 1 from appropriate starting materials. In Examples 2 and 3, thionyl chloride was added to a solution of the starting alcohol and imidazole, and in Example 2, water and ethyl acetate were used in the extraction procedure in place of, respectively, sodium bicarbonate and dichloromethane.

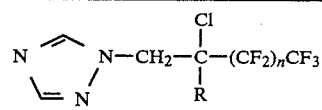

| Example No. | R | n | % Yield | m.p. (°C.) | Analysis % (Theoretical in brackets) C | H | N |
|---|---|---|---|---|---|---|---|
| 2 | 4-Cl-C₆H₄ | 0 | 85 | 62–64 | 42.7 (42.6 | 2.7 2.6 | 13.7 13.5) |
| 3 | 4-F-C₆H₄ | 0 | 42 | 75–77 | 44.9 (45.0 | 2.6 2.7 | 14.1 14.3) |
| 4 | 4-F-C₆H₄ | 1 | 57 | 110–113 | 42.3 (41.9 | 2.3 2.4 | 12.3 12.2) |
| 5 | 2,4-F₂-C₆H₃ | 2 | 51 | 74–76 | 38.0 (37.9 | 1.7 1.7 | 10.0 10.2) |

EXAMPLE 6

By employing thionyl bromide in place of the thionyl chloride used in the preceding Examples the following compounds are obtained in like manner.

1-[2-bromo-2-(2,4-difluorophenyl)-3,3,3-trifluoropropyl]-1H-1,2,4-triazole,

1-[2-bromo-2-(4-chlorophenyl)-3,3,3-trifluoropropyl]-1H-1,2,4-triazole,

1-[2-bromo-2-(4-fluorophenyl)-3,3,3-trifluoropropyl]-1H-1,2,4-triazole,

1-[3-bromo-3-(4-fluorophenyl)-1,1,1,2,2-pentafluorobutan-4-yl]-1H-1,2,4-triazole, and 1-[4-bromo-4-(2,4-difluorophenyl)-1,1,1,2,2,3,3-heptafluoropenta-5-yl]-1H-1,2,4-triazole.

EXAMPLE 7

When the starting alcohols used in Examples 1–5 are reacted with diethylaminosulfur trifluoride in methylene chloride at 0° C. and the resulting product isolated and purified as described above for the compounds of formula (I), X=Cl, the corresponding compounds are obtained wherein X is F and n and R are as defined for the starting alcohol.

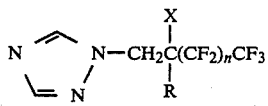

(I)

EXAMPLE 8

Using the appropriate alcohol as starting material in the procedures of Example 1 provides the corresponding compounds of the formula below where R is as defined below.

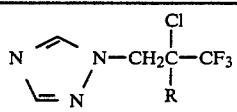

| R | R |
|---|---|
| 4-CF$_3$C$_6$H$_4$ | 2,4-Cl$_2$C$_6$H$_3$ |
| 2F,4-ClC$_6$H$_3$ | 2,5F$_2$C$_6$H$_3$ |
| 2,4,6-F$_3$C$_6$H$_2$ | 4-Br,2,5-F$_2$C$_6$H$_2$ |

EXAMPLE 9

Similarly, the compounds below are prepared by the methods of the preceding Examples by employing the appropriate starting alcohol.

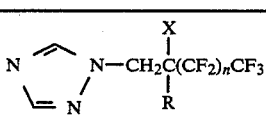

(I)

| n | X | R |
|---|---|---|
| 0 | Br | 2-CF$_3$C$_6$H$_4$ |
| 0 | F | 3-CF$_3$C$_6$H$_4$ |
| 0 | Cl | 5-chloro-2-pyridyl |
| 0 | F | 2,4,6-F$_3$C$_6$H$_2$ |
| 1 | Cl | 4-CF$_3$C$_6$H$_4$ |
| 1 | Cl | 5-chloro-2-pyridyl |
| 1 | Br | 5-chloro-2-pyridyl |
| 1 | F | 2-CF$_3$C$_6$H$_4$ |
| 1 | Cl | 2,4-Cl$_2$C$_6$H$_3$ |
| 1 | F | 2,4-F$_2$C$_6$H$_3$ |
| 2 | F | 2,4,6-F$_3$C$_6$H$_2$ |
| 2 | Cl | 2-F,4-ClC$_6$H$_3$ |
| 2 | Cl | 5-chloro-2-pyridyl |
| 2 | Cl | 4-CF$_3$C$_6$H$_4$ |
| 2 | Br | 4-FC$_6$H$_4$ |
| 2 | Br | 2,5-F$_2$C$_6$H$_3$ |
| 3 | Cl | 4-CF$_3$C$_6$H$_4$ |
| 3 | Cl | 2-CF$_3$C$_6$H$_4$ |
| 3 | F | 5-chloro-2-pyridyl |
| 3 | Br | 5-chloro-2-pyridyl |
| 3 | Br | 4-Br,2,5-F$_2$C$_6$H$_2$ |
| 4 | Cl | 4-FC$_6$H$_4$ |
| 4 | Cl | 4-ClC$_6$H$_4$ |
| 4 | Cl | 4-CF$_3$C$_6$H$_4$ |
| 4 | Cl | 2,4-Cl$_2$C$_6$H$_3$ |
| 4 | Br | 2,4-F$_2$C$_6$H$_3$ |
| 4 | F | 2,4-Cl$_2$C$_6$H$_4$ |
| 4 | Cl | 5-chloro-2-pyridyl |
| 4 | F | 2,4,6-F$_3$C$_6$H$_2$ |
| 5 | Cl | 4-FC$_6$H$_4$ |
| 5 | Cl | 4-ClC$_6$H$_4$ |
| 5 | Cl | 2,4-Cl$_2$C$_6$H$_3$ |
| 5 | Cl | 2,4-F$_2$C$_6$H$_3$ |
| 5 | F | 4-CF$_3$C$_6$H$_4$ |
| 5 | Br | 5-chloro-2-pyridyl |
| 5 | Cl | 5-chloro-2-pyridyl |

EXAMPLE 10

The following illustrate pharmaceutical compositions for the treatment of fungal infections:

(a) Capsule: 71 parts by weight of the compound of Example 1 are granulated with 3 parts maize starch and 22 parts lactose and then a further 3 parts maize starch and 1 part magnesium stearate are added. The mixture is regranulated and filled into hard gelatin capsules.

(b) Cream: 2 parts by weight of the compound of Example 5 are dissolved in 10 parts of propylene glycol and mixed into 88 parts of a vanishing cream base.

(c) Pessary: 2 parts by weight of the compound of Example 3 are suspended in 98 parts of a warm liquified suppository base which is poured into moulds and allowed to solidify.

PREPARATION A 2-(2,4-Difluorophenyl)-1-(1H-1,2,4-triazol-1-yl)-3,3,3-trifluoropropan-2-ol

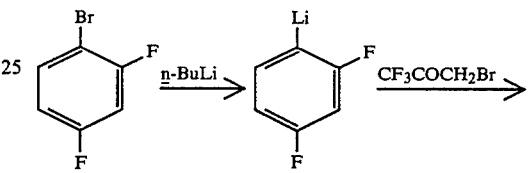

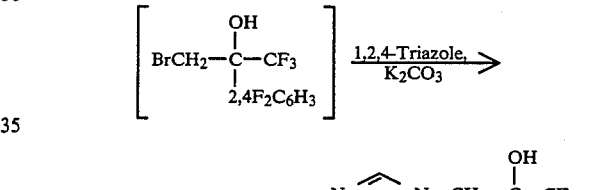

A hexane solution of n-butyllithium (1.55M, 9.6 ml, 14.9 mmole) was added to diethylether (6 ml) and the solution was cooled to −78° C. A solution of 2,4-difluorobromobenzene (3.03 g, 15.7 mmole) in diethylether (100 ml) was added dropwise over 15 minutes and the mixture was stirred at −78° C. for a further 15 minutes. A solution of 1-bromo-3,3,3-trifluoropropan-2-one (2.4 g, 12.6 mmole) in diethylether (100 ml) was then added dropwise over 15 minutes and the mixture was stirred at −78° C. for a further 30 minutes. A solution of glacial acetic acid (2 ml) in diethylether (5 ml) was then added, followed by water (15 ml) and the mixture was allowed to warm to 0° C. The aqueous layer was separated and washed with diethylether (2×30 ml). The combined diethylether extracts were dried over magnesium sulphate, evaporated, and the residual oil was dissolved in dimethylformamide (40 ml). 1,2,4-Triazole (2.5 g, 36.2 mmole) and anhydrous potassium carbonate (10 g, 72.5 mmole) were then added to this solution and the mixture was stirred and heated at 70° C. for 18 hours. The mixture was then cooled, poured into water (150 ml) and extracted with ethyl acetate (3×100 ml). The combined ethyl acetate extracts were washed with water (100 ml), dried over magnesium sulphate, and evaporated. The residue was chromatographed on silica (230–400 mesh), eluting with ethyl acetate:hexane, 60:40 by volume, to give, after one recrystallization from ethyl acetate/hexane, the title compound, 1.7 g (47%), m.p. 110°–111° C.

Analysis %: Found: C, 45.2; H, 2.7; N, 14.6. $C_{11}H_8F_5N_3O$ requires: C, 45.0; H, 2.7; N, 14.3.

PREPARATION B

The following compounds were prepared by the above method from the appropriate starting materials:

$$\underset{R}{\underset{|}{N}}\text{-triazole-}N-CH_2\underset{|}{\overset{OH}{\underset{|}{C}}}-CF_3$$

| R | % Yield | m.p. (°C.) | C | H | N |
|---|---|---|---|---|---|
| 2-Br-4,5-diF-phenyl | 67 | 148–50 | 35.90 (35.51 | 1.93 1.90 | 11.42 11.29) |
| 4-CF₃-phenyl | 21 | 94–96 | 44.36 (44.32 | 2.76 2.79 | 13.13 12.92) |
| 4-F-phenyl | 23 | 134–6 | 47.78 (48.00 | 3.20 3.30 | 15.49 15.27) |
| 2,4,6-triF-phenyl | 10 | 89–91 | 42.77 (42.46 | 2.27 2.27 | 13.88 13.50) |
| 2,4-diF-phenyl* | 50 | 144–147 | 37.19 (37.02 | 3.04 3.11 | 10.67 10.79) |
| 4-Cl-2-F-phenyl | 0.4 | 95 | 43.4 (42.7 | 2.7 2.6 | 13.0 13.6) |

*as methanesulphonate salt

PREPARATION C 2-(4-Chlorophenyl)-1-(1H-1,2,4-triazol-1-yl)-3,3,3-trifluoropropan-2-ol $$CF_3-\overset{O}{\overset{\|}{C}}-\underset{}{\text{C}_6\text{H}_4}-Cl \xrightarrow[\text{1,1,1-trichloroethane.}]{\text{Trimethylsulphoxonium iodide,}\atop\text{cetrimide, aqueous NaOH,}}$$

(known)

$$\left[\begin{array}{c} CF_3-\overset{O}{\underset{\bigtriangleup}{C}}-CH_2 \\ | \\ \text{4-Cl-C}_6\text{H}_4 \end{array}\right]$$

$$\xrightarrow{\text{1,2,4-triazole, }K_2CO_3,\text{ DMF.}}$$

$$\underset{\text{4-Cl-C}_6\text{H}_4}{\overset{OH}{\underset{|}{CF_3-\underset{|}{C}-CH_2-N}}}\text{-triazole}$$

2,2,2-Trifluoro-4′-chloroacetophenone (0.8 g, 3.84 mmole), trimethylsulphoxonium iodide (1.02 g, 4.6 mmole) and cetyltrimethylammonium bromide (0.1 g, 0.27 mmole) were stirred in a mixture of 1,1,1-trichloroethane (40 ml) and 18% sodium hydroxide solution (20 ml) at 75° for 2 hours. The mixture was then allowed to cool, the organic layer was separated, evaporated, and the residue was stirred in dimethylformamide (50 ml) with 1,2,4-triazole (1 g, 14.5 mmole) and anhydrous potassium carbonate (2 g, 14.5 mmole) at 90° for 4 hours. The mixture was then allowed to cool, ethyl acetate (100 ml) and water (50 ml) were added and the aqueous layer was separated. The organic layer was washed a further 6 times with water (200 ml in total), dried over magnesium sulphate, and evaporated to give a gum (104 mg) which was chromatographed on silica (230–400 mesh), eluting with ethyl acetate to give as a colorless solid the title compound, 84 mg (8%). One recrystallization from dichloromethane/hexane gave colorless crystals, 64 mg, m.p. 117°–118° C.

Analysis %: Found: C, 45.4; H, 3.1; N, 14.8. Required for $C_{11}H_9ClF_3N_3O$: C, 45.23; H, 3.1; N, 14.4.

PREPARATION D 2-(2,4-Dichlorophenyl)-1-(1H-1,2,4-triazol-1-yl)-3,3,3-trifluoropropan-2-ol

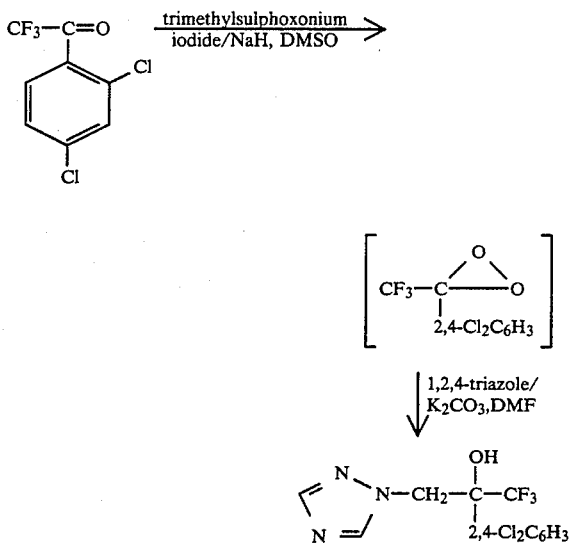

Sodium hydride as a 60% oil dispersion (0.36 g, 9.05 mmole) was washed with distilled hexane, dried, and stirred at room temperature with trimethylsulphoxonium iodide (1.99 g, 9.05 mmole). Dimethylsulphoxide (10 ml) was then added dropwise over five minutes and the mixture was stirred until effervescense had ceased (about 30 minutes). A solution of 2',4'-dichloro-2,2,2-trifluoroacetophenone (2 g, 8.23 mmole) in dimethylsulphoxide (8 ml) was then added and the mixture was stirred at room temperature for 45 minutes. Water (50 ml) and ether (100 ml) were then added and the organic layer was separated, washed once with water, dried over magnesium sulphate and evaporated to give a pale yellow liquid (1.8 g) which was added to a mixture of 1,2,4-triazole (2 g, 29 mmole) and anhydrous potassium carbonate (4 g, 29 mmole) in dimethylformamide (100 ml). This mixture was heated at about 75° C. for 18 hours and then poured into a mixture of ethyl acetate (500 ml) and water (200 ml). The organic layer was separated, washed with water (5×100 ml), dried over magnesium sulphate, and evaporated to give a pale yellow tacky solid which was chromatographed on silica (230–400 mesh) eluting with ethyl acetate, to give, after recrystallization from ethyl acetate, the title compound, 1.49 g (56%), m.p. 133.5°-134.5° C.

Analysis %: Found: C, 40.58; H, 2.58; N, 12.96. Required for $C_{11}H_8Cl_2F_3N_3O$: C, 40.49; H, 2.45; N, 12.88.

PREPARATION E

The following compounds were prepared by the method of Preparation A using n-butyllithium, 4-fluorobromobenzene and either 1-bromo-3,3,3-trifluoropropan-2-one or 1-bromo-3,3,4,4,4-pentafluorobutan-2-one.

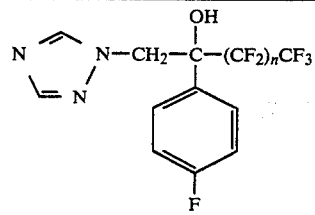

| n | m.p. (°C.) | Analysis % (Theoretical in Brackets) | | |
|---|---|---|---|---|
| | | C | H | N |
| 0 | 134–136° | 47.8 | 3.2 | 15.5 |
| | | (48.0 | 3.3 | 15.3) |
| 1 | 95–97° | 44.6 | 2.8 | 13.3 |
| | | (44.3 | 2.8 | 12.9) |

PREPARATION F 2-(2,4-Difluorophenyl)-1,1,1,2,2,3,3-heptafluoro-5-(1H-1,2,4-triazol-1-yl)pentan-4-ol

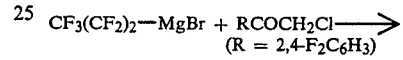

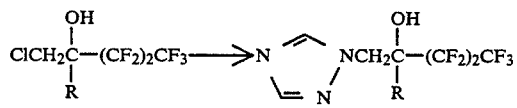

To a solution of heptafluoropropyl iodide (5 g, 0.017 mole) in ethyl ether (20 ml) cooled to −78° C., was added phenylmagnesium bromide (5.6 ml of a 3 molar solution in ethyl ether, 0.017 mole) dropwise at such a rate that the temperature of the reaction mixture did not exceed −50° C. When all the phenylmagnesium bromide had been added, the mixture was stirred at −50° C. for a half hour and then cooled again to −78° C. A solution of 2-chloro-2',4'-difluoroacetophenone (3.6 g, 0.019 mole) in ether (20 ml) was added dropwise at such a rate that the temperature of the reaction mixture did not exceed −50° C. When the addition was complete, the reaction mixture was allowed to warm to −20° C. and was stirred at this temperature for 2 hours. A solution of glacial acetic acid (3 ml) in ether (5 ml) was then added, followed by water (15 ml) and the mixture was allowed to warm to about 5° C. The aqueous phase was separated, extracted with ether (2×50 ml), the combined ether extracts were dried (MgSO4) and evaporated to give a pale yellow oil (6.7 g). This oil was added to a mixture of 1,2,4-triazole (5.87 g, 0.085 mole) and anhydrous potassium carbonate (17.5 g, 0.127 mole) in dimethylformamide (60 ml) and this mixture was stirred at a temperature of 80° C. for 3 hours. The reaction mixture was then cooled, the dimethylformamide was evaporated and the residue was partitioned between water (200 ml) and ethyl acetate (150 ml). The aqueous layer was separated and extracted with ethyl acetate (3×150 ml). The combined ethyl acetate extracts were washed successively with aqueous sodium bisulphite and water, dried (MgSO4), evaporated and the residue was flash chromatographed on silica (230–400 mesh), eluting with a mixture of hexane:isopropyl alcohol:0.88 ammonium hydroxide, 80:20:1.5 by volume, to yield, after one recrystallization from hexane:dichloromethane, the title compound, 1.51 g (23%), m.p. 128°–129° C.

Analysis %: Found: C, 39.8; H, 2.0; N, 10.6. Required for $C_{13}H_8F_9N_3O$: C, 39.7; H, 2.1; N, 10.7.

We claim:

1. A compound of the formula

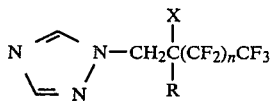

(I)

or a pharmaceutically or agriculturally acceptable acid addition salt thereof, wherein R is 5-chloro-2-pyridyl, trifluoromethylphenyl or phenyl substituted by 1 to 3 substituents each independently selected from F, Cl and Br; n is zero or an integer of from 1 to 5; and X is F, Cl or Br.

2. A compound according to claim 1 wherein X is Cl.

3. A compound according to claim 1 wherein n is zero, 1 or 2.

4. A compound according to claim 1, wherein R is 4-fluorophenyl, 4-chlorophenyl, 4-trifluoromethylphenyl, 2,4-dichlorophenyl, 2,4-difluorophenyl, 2,5-difluorophenyl, 2-fluoro-4-chlorophenyl, 2,4,6-trifluorophenyl or 4-bromo-2,5-difluorophenyl.

5. A compound as claimed in claim 4, wherein R is 2,4-difluorophenyl, 4-chlorophenyl or 4-fluorophenyl, X is Cl and n is zero, 1 or 2.

6. The compound according to claim 5: 1-[2-chloro-2-(2,4-difluorophenyl)-3,3,3-trifluoropropyl]-1H-1,2,4-triazole.

7. The compound according to claim 5: 1-[2-chloro-2-(4-chlorophenyl)-3,3,3-trifluoropropyl]-1H-1,2,4-triazole.

8. The compound according to claim 5: 1-[2-chloro-2-(4-fluorophenyl)-3,3,3-trifluoropropyl]-1H-1,2,4-triazole.

9. The compound according to claim 5: 1-[3-chloro-3-(4-fluorophenyl)-1,1,1,2,2-pentafluorobutan-4-yl]-1H-1,2,4-triazole.

10. The compound according to claim 5: 1-[4-chloro-4-(2,4-difluorophenyl)-1,1,1,2,2,3,3-heptafluoropentan-5-yl]-1H-1,2,4-triazole.

11. A pharmaceutical composition comprising an antifungal amount of a compound or pharmaceutically acceptable salt thereof according to claim 1 and a pharmaceutically acceptable diluent or carrier.

12. An agricultural antifungal composition suitable for use on a plant or seed which comprises an antifungal amount of a compound or agriculturally acceptable salt thereof according to claim 1 and an agriculturally acceptable diluent or carrier.

13. A method of treating a fungal infection in an animal in need of such treatment which comprises administering to said animal an antifungal amount of a compound or pharmaceutically acceptable salt thereof according to claim 1.

14. A method of treating a fungal infection in a plant or seed in need of such treatment which comprises administering to said plant or seed an antifungal amount of a compound or agriculturally acceptable salt thereof according to claim 1.

* * * * *